United States Patent [19]

Kolich et al.

[11] Patent Number: 4,698,439
[45] Date of Patent: Oct. 6, 1987

[54] MIXED ESTERS OF POLYPHOSPHAZENES

[75] Inventors: Charles H. Kolich; W. Dirk Klobucar, both of Baton Rouge, La.

[73] Assignee: Ethyl Corporation, Richmond, Va.

[21] Appl. No.: 862,000

[22] Filed: May 12, 1986

[51] Int. Cl.$^4$ .............................................. C07F 9/00
[52] U.S. Cl. ...................................... 558/80; 252/78.5
[58] Field of Search ........................................... 558/80

[56] References Cited

U.S. PATENT DOCUMENTS 3,291,865 12/1966 Kober et al. ........................... 558/80
4,600,791 7/1986 Carr et al. ............................. 558/80
4,601,843 7/1986 Carr et al. ........................... 252/78.5

FOREIGN PATENT DOCUMENTS 0145002 6/1985 European Pat. Off. .

OTHER PUBLICATIONS

Lederle et al., J. Chem. & Eng. Data, vol. 11, No. 2, Apr, 1966, pp. 221-228.
Ottmann et al., Ind. & Eng. (Chem. Prod. Res. & Dev.), vol. 5, No. 2, Jun. 1966, pp. 202-204.
Singler et al, (I), "Army Science Conference Paper", A117298.
Singler, "Potential of Phosphazenes as Hydraulic Fluids", Hydraulic Fluids Meeting, NASA, Ames Research Center, Feb. 1976.
Singler et al. (II), Ind. & Eng. (Chem. Prod. Res. & Dev.), vol. 25, No. 1, 1986, pp. 46-57.

Primary Examiner—Anton H. Sutto
Attorney, Agent, or Firm—Donald L. Johnson; John F. Sieberth; J. D. Odenweller

[57] ABSTRACT

A polyphosphazene hydraulic fluid that remains solids-free on storage at temperatures down to $-30°$ C. over an extended period can be made by reacting a solution of sodium phenoxide, sodium m-methylphenoxide, sodium p-methylphenoxide and sodium trifluoroethoxide with a small stoichiometric excess of cyclic phosphonitrilic chloride oligomer, mainly trimer, and then reacting the remaining replaceable chlorine atoms with a solution of sodium trifluoroethoxide.

16 Claims, No Drawings

MIXED ESTERS OF POLYPHOSPHAZENES

BACKGROUND OF THE INVENTION

Hydraulic fluids are used to transfer energy through fluid conduits to cause a force to be exerted against a moveable object (e.g. a piston) resulting in work. In order to function efficiently, it is necessary that such fluids be stable and preferably fire resistant. A very important property is that the fluid have a low pour point and that it does not form any solid precipitate when maintained at low temperature for an extended period. Solids could plug orifices and cause a malfunction in the hydraulic system.

Because of their fire resistance, polyphosphazenes have been investigated for some time in an attempt to prepare a suitable hydraulic fluid. Kober et al., U.S. Pat. No. 3,291,865 describes the preparation of hydraulic fluids by reacting mixtures of phenols or substituted phenols and fluoroalcohols with cyclic phosphonitrilic chloride trimer.

Lederle et al., J. Chem. & Eng. Data, Vol. 11, No. 2, April 1966, page 221 describes fire resistant hydraulic fluids made in a manner similar to Kober et al. Ottmann et al., Ind. & Eng. (Chem. Prod. Res. & Dev.), Vol. 5, No. 2, June 1966, page 202 describe arylamino polyfluoroalkoxy-substituted phosphonitrilic cyclic trimers made by the addition of N-methylaniline and triethylamine to a stoichiometric excess of phosphonitrilic chloride trimer. This in turn is then added to a solution of sodium fluoroalkoxide to complete the reaction.

Singler et al., "Army Science Conference Paper", A117298 describe the synthesis and evaluation of phosphazene fluid in an attempt to find a replacement for triarylphosphates under military specification MIL-H-19457c. This research involved the use of trifluoroethoxy-substituted cyclic phosphonitrilates which were also substituted with either m-chlorophenoxy or m-trifluoromethylphenoxy groups. Three modes of synthesis are described:
(1) addition of trimer to a mixture of sodium aryloxide and sodium trifluoroethoxide,
(2) addition of a mixture of sodium aryloxide and trifluoroethoxide to trimer, and
(3) sequential addition of sodium aryloxide followed by sodium trifluoroethoxide to trimer.

Crystallization appears to have been encountered in all cases but oil recovery was increased by following the methods of modes two or three.

Singler, "Potential of Phosphazenes as Hydraulic Fluids", Hydraulic Fluids Meeting, NASA Ames Research Center, February 1976 summarizes the effect of various substituents on the substituted cyclic phosphonitrilate trimers and tetramers.

More recently, Singler et al., Ind. Eng. Chem. (Prod. Res. & Dev.), Vol. 25, No. 1 (1986) describe hydraulic fluids made by substituting cyclic phosphonitrilic chloride with both aryloxy groups and trifluoroethoxy groups. Reference is again made to the three modes of synthesis; "which yielded widely different ratios of solids to fluids". For example, mode two in which an equal mole mixture of sodium m-chlorophenate and sodium trifluoroethoxide was added to trimer increased the oil recovery from 18% up to 62%.

Carr, Eur. Pat. Appl. No. 0 145 002, published June 19, 1985 discloses a phosphazene fluid prepared by reacting cyclic phosphonitrilic chloride trimer with a phenol, a polyfluoroalcohol or mixtures thereof in a two-phase medium comprising water and a water-immiscible solvent. The reaction is promoted by use of a base, e.g. sodium hydroxide, and a phase transfer catalyst. In Example 4, the process carried out with trifluoroethanol and phenol is said to form an almost colorless clear liquid.

SUMMARY OF THE INVENTION

It has now been discovered that a clear substantially solids-free polyphosphazene hydraulic fluid can be made by reacting a mixture of sodium phenoxide, sodium m-methylphenoxide, sodium p-methylphenoxide and sodium trifluoroethoxide with a slight stoichiometric excess of cyclic phosphonitrilic chloride trimer followed by a second stage in which residual chlorine substituents are reacted with a second quantity of sodium trifluoroethoxide. The recovered fluid remains solids-free on cold storage cycling between $-10°$ and $-30°$ C.

DESCRIPTION OF THE PREFERRED EMBODIMENTS

A preferred embodiment of the invention is a process for making a polyphosphazene hydraulic fluid that remains solids-free on storage at temperatures down to $-30°$ C., said process comprising:
(A) preparing a solution of about 0.2–0.3 mole parts of sodium phenoxide, 0.12–0.22 mole parts of sodium m-methylphenoxide, 0.02–0.15 mole parts of sodium p-methylphenoxide and 0.3–0.9 mole parts of sodium 2,2,2-trifluoroethoxide in an inert solvent, the total parts being about 0.85–0.95 moles for each equivalent of replaceable chlorine in the cyclic phosphonitrilic chloride oligomer,
(B) preparing a solution of about 0.2 mole parts of a cyclic phosphonitrilic chloride oligomer comprising predominantly trimer in an inert solvent,
(C) mixing the solution of step (A) with the solution of step (B),
(D) reacting the resultant mixture until the reaction is substantially complete,
(E) preparing a solution of sodium 2,2,2-trifluoroethoxide in an inert solvent,
(F) in a second stage, mixing the trifluoroethoxide solution of step (E) with the reaction mixture of step (D), the amount of said trifluoroethoxide solution being an amount which when taken together with the sodium phenoxide, m-methylphenoxide, p-methylphenoxide and trifluoroethoxide of step (A), totals at least 1.01 mole parts per each equivalent of replaceable chlorine in said cyclic phosphonitrilic chloride oligomer,
(G) reacting the mixture until substantially all replaceable chlorine has reacted and
(H) recovering the polyphosphazene hydraulic fluid.

More preferably, the total amount of sodium phenoxide, sodium m-methylphenoxide, sodium p-methylphenoxide and sodium 5 trifluoroethoxide that added in the second stage is at least 1.05 moles per each equivalent of replaceable chlorine in the cyclic phosphonitrilic chloride trimer (hereinafter referred to as "trimer") in the initial charge. A still more preferred total amount of aryloxide and trifluoroethoxide is about 1.01–1.05 mole parts per each equivalent of replaceable chlorine in the trimer charge. One mole of trimer contains six equivalents of replaceable chlorine.

In a more preferred embodiment, the composition of the solution used in step (A) comprises about 0.23–0.27 mole parts of sodium phenoxide, 0.15-0.2 mole parts of sodium m-methylphenoxide, 0.05-0.11 mole parts of p-methylphenoxide and 0.5-0.7 mole parts of sodium trifluoroethoxide.

In the most preferred embodiment, the hydraulic fluid is prepared by:

(A) preparing a solution of about 0.25 moles of sodium phenoxide, 0.18 moles of sodium m-methylphenoxide, 0.08 moles of sodium p-methylphenoxide and 0.6 moles of sodium 2,2,2-trifluoroethoxide in tetrahydrofuran, (B) preparing a solution of about 0.2 mole parts of cyclic phosphonitrilic chloride trimer in cyclohexane, (C) adding the solution of step (A) to the solution of step (B) over an extended period of time, (D) heating the resultant mixture at reflux, (E) preparing a solution of about 0.13 mole parts of sodium 2,2,2-trifluoroethoxide in tetrahydrofuran, (F) mixing the solution of step (E) with the reaction mixture of step (D), (G) heating the mixture at reflux until substantially all replaceable chlorine has reacted and (H) recovering the polyphosphazene hydraulic fluid.

The inert solvent used in step (A) and (E) can be any inert solvent in which the aryloxides and the trifluoroethoxides are soluble. The sodium salts are soluble in most ethers such as diethyl ether, dioxane, tetrahydrofuran (THF), dimethoxyethane, diethylene glycol dimethyl ether and the like. The preferred ether solvent is THF.

The amount of solvent used in steps (A) and (E) should be an amount sufficient to dissolve the aryloxides and trifluoroethoxide. A useful range is about 200-500 parts by weight solvent per 100 parts sodium aryloxide and sodium trifluoroethoxide. A more useful range when using THF is about 250-300 parts THF per each 100 parts sodium aryloxide and sodium trifluoroethoxide.

The inert solvent used to dissolve the trimer in step (B) can be any solvent that is substantially inert to the trimer and to the sodium aryloxide and sodium trifluoroethoxide. These can include aromatic hydrocarbons, cycloalkanes, haloalkanes, haloaromatics and the like. Representative examples are benzene, toluene, xylene, cyclohexane, methyl cyclohexane, sym-tetrachloroethane, 1,1,1-trichloroethane, carbon tetrachloride, chlorobenzene, chlorotoluene, di-chlorobenzene, di-chlorotoluene and the like including mixtures thereof. The most preferred solvent for the trimer is cyclohexane.

The amount of trimer solvent used in step (B) should be a solvent amount. A useful range is about 3-10 parts of solvent per each part by weight trimer. With cyclohexane, good results have been achieved using about 4 parts cyclohexane per part trimer.

The trimer used in the process need not be pure trimer. Trimer is made by reacting phosphorus pentachloride with ammonium chloride in a solvent such as monochlorobenzene at or near reflux. An excess of ammonium chloride favors cyclics. After removal of solids and linears, the cyclic oligomers are predominantly trimer (e.g. 75-90 weight percent trimer) with lesser amounts of tetramers and higher cyclics. The trimer can be purified by distillation and/or crystallization. Extensive purification is not required and the trimer can contain minor amounts of tetramer (e.g. up to 10 weight percent and preferably less than 5 weight percent).

The sodium aryloxides can be made by reacting sodium metal in an ether solvent with a mixture of phenol, m-cresol and p-cresol in the desired ratio. The reaction proceeds readily at room temperatures but may be conducted up to reflux.

The sodium trifluoroethoxide can be prepared by carefully adding sodium dispersion to an ether solution of trifluoroethanol. A suitable process is described in Sulzer et al., U.S. Pat. No. 4,568,779. Since metallic sodium can react with the fluorine substituents, (Wurz reaction) it is important to minimize the amount of unreacted sodium present in the system at any one time.

The ether solution of the aryloxides and trifluoroethoxides is added to the trimer solution over an extended period. The purpose of this is to always maintain an excess of trimer so that the desired group distribution occurs. Depending upon reaction scale, this addition can take from about 5 minutes up to 8 hours or more.

At the start of the addition, the trimer solution is preferably at ambient temperature. The heat of reaction causes the temperature to rise during the addition. Heat is supplied towards the end of the reaction to bring the mixture to reflux. With a THF-cyclohexane system this is about 71° C. Reflux is continued until the reaction is substantially complete. Reflux is not necessary to complete the reaction since it will go to completion at lower temperatures over a longer time period. Since the total mole parts of aryloxide and trifluoroethoxide is about 0.85-0.95 per each equivalent of replaceable chlorine in the trimer, there will still remain about 0.05-0.15 equivalents of replaceable chlorine in the reaction mixture.

In a second stage, a solution of sodium trifluoroethoxide is prepared in an inert solvent and this is mixed with the first reaction mixture. The amount of sodium trifluoroethoxide used in this stage is sufficient to react with the remaining chlorine atoms. Preferably the total amount of aryloxide and trifluoroethoxide used in the overall process is at least about 1.01 moles per each equivalent of chlorine in the initial trimer charge. A useful range is about 1.01-1.05 mole parts aryloxide and trifluoroethoxide per each equivalent of chlorine.

The second stage reaction mixture is then heated to complete the substitution reaction. Preferably it is refluxed for about 15 minutes up to an hour.

The hydraulic fluid preparation is then complete and it can be recovered by any conventional procedure that removes solvents and salt byproducts. In a preferred procedure the mixture is first washed with water and the water layer removed. Next the mixture is washed with 5% aqueous caustic followed by a second water wash. Residual solvent is then distilled out under vacuum leaving the hydraulic fluid. The final fluid may be filtered if there are any solids present.

The following example shows how the hydraulic fluid can be prepared.

EXAMPLE

In a dry reaction vessel was placed 69.48 grams (0.2 moles) phosphonitrilic chloride trimer (97.4 mole percent trimer, 2.6 mole percent tetramer) and 282 grams of cyclohexane. Following this, 385 grams of a THF solution containing 29.5 grams (0.25 moles) sodium phenoxide, 22.9 grams (0.18 moles) sodium m-methylphenoxide, 9.96 grams (0.077 moles) of sodium p-methylphenoxide and 73.1 grams (0.6 moles) sodium 2,2,2-trifluoroethoxide was added over a 25 minute period as the temperature climbed from 29° C. up to 62° C. The mixture was then heated to reflux (71° C.) and held at reflux for 1 hour. Following this, a solution of 0.13 moles of sodium trifluoroethoxide in tetrahydrofuran was added and the mixture refluxed for 70 minutes. Following this, the mixture was washed with about 250 grams of water and the water layer removed. The mixture was then washed with 5% aqueous caustic. Following this, the mixture was washed a second time with water. The mixture was transferred to a distillation apparatus and solvents were distilled out under vacuum up to a liquid temperature of 70° C. at 1–2 torr. This yielded 144.7 grams of a clear fluid.

The U.S. Navy has established certain criteria for phosphazene hydraulic fluids. These are published in "Information to Offerors Or Quoters" Solicitation No. N00167-86-R-0065. These physical properties compare to those of the hydraulic fluid prepared above are as follows:

|  | Navy Spec. | Percent Fluid |
| --- | --- | --- |
| Appearance | clear, colorless |  |
| Viscosity (40°) | 32–38 cSt | 38.1 cSt |
| (100°) | 3.7 cSt min. | 4.4 cSt |
| Pour Point | −21° C. max. | −21° C. |
| Density | 1.5 g/ml max. | 1.446 |
| Acid No. | 0.1 mg KOH/g |  |
| Demulsibility | 40/40 3 min. separation |  |
| Flash Point | 275° C. |  |

The fluid was placed in a cold box which cycled between −30° C. and −10° C. After ten weeks the fluid remained clear and solids-free.

The present process provides a hydraulic fluid having excellent physical properties which remain solids-free after extended storage at very low temperatures.

We claim:

1. A process for making a polyphosphazene hydraulic fluid that remains solids-free on storage at temperatures down to −30° C., said process comprising:

(A) preparing a solution of about 0.2–0.3 mole parts of sodium phenoxide, 0.12–0.22 mole parts of sodium m-methylphenoxide, 0.02–0.15 mole parts of sodium p-methylphenoxide and 0.3–0.9 mole parts of sodium 2,2,2-trifluoroethoxide in an inert solvent, the total parts being about 0.85–0.95 moles for each equivalent of replaceable chlorine in the cyclic phosphonitrilic chloride oligomer, (B) preparing a solution of about 0.2 mole parts of a cyclic phosphonitrilic chloride oligomer comprising predominantly trimer in an inert solvent, (C) mixing the solution of step (A) with the solution of step (B), (D) reacting the resultant mixture at a temperature in the range of ambient up to reflux until the reaction is substantially complete, (E) preparing a solution of sodium 2,2,2-trifluoroethoxide in an inert solvent, (F) in a second stage, mixing the trifluoroethoxide solution of step (E) with the reaction mixture of step (D), the amount of said trifluoroethoxide solution being an amount which when taken together with the sodium phenoxide, m-methylphenoxide, p-methylphenoxide and trifluoroethoxide of step (A), totals at least 1.01 mole parts per each equivalent of replaceable chlorine in said cyclic phosphonitrilic chloride oligomer, (G) reacting the mixture at an elevated temperature up to reflux until substantially all replaceable chlorine has reacted and (H) recovering the polyphosphazene hydraulic fluid.

2. A process of claim 1 wherein in step (C) the solution of step (A) is added to the solution of step (B).

3. A process of claim 2 wherein said inert solvent in steps (A) and (E) is an ether.

4. A process of claim 3 wherein said inert solvent in step (B) is cyclohexane.

5. A process of claim 1 wherein the amount of trifluoroethoxide solution added in step (F) is an amount which when taken together with the sodium phenoxide, m-methylphenoxide, p-methylphenoxide and trifluoroethoxide of step (A) totals about 1.01–1.05 mole parts per each equivalent of replaceable chlorine in said cyclic phosphonitrilic chloride oligomer.

6. A process of claim 5 wherein in step (C) the solution of step (A) is added to the solution of step (B) over an extended period of time.

7. A process of claim 6 wherein said inert solvent in steps (A) and (E) is tetrahydrofuran and said inert solvent in step (B) is cyclohexane.

8. A process of claim 7 wherein the solution in step (A) comprises 0.23–0.27 mole parts of sodium phenoxide, 0.15–0.2 mole parts of sodium m-methylphenoxide, 0.05–0.11 mole parts of sodium p-methylphenoxide and 0.5–0.7 mole parts of sodium 2,2,2-trifluoroethoxide.

9. A process for making a polyphosphazene hydraulic fluid that remains solids-free on storage at −30° C., said process comprising:

(A) preparing a solution of about 0.25 moles of sodium phenoxide, 0.18 moles of sodium m-methylphenoxide, 0.08 moles of sodium p-methylphenoxide and 0.6 moles of sodium 2,2,2-trifluoroethoxide in tetrahydrofuran, (B) preparing a solution of about 0.2 mole parts of cyclic phosphonitrilic chloride trimer in cyclohexane, (C) adding the solution of step (A) to the solution of step (B) over an extended period of time, (D) heating the resultant mixture at reflux, (E) preparing a solution of about 0.13 mole parts of sodium 2,2,2-trifluoroethoxide in tetrahydrofuran, (F) mixing the solution of step (E) with the reaction mixture of step (D), (G) heating the mixture at reflux until substantially all replaceable chlorine has reacted and (H) recovering the polyphosphazene hydraulic fluid.

10. A polyphosphazene hydraulic fluid made by the process of claim 1.

11. A polyphosphazene hydraulic fluid made by the process of claim 2.

12. A polyphosphazene hydraulic fluid made by the process of claim 5.

13. A polyphosphazene hydraulic fluid made by the process of claim 6.

14. A polyphosphazene hydraulic fluid made by the process of claim 7.

15. A polyphosphazene hydraulic fluid made by the process of claim 8.

16. A polyphosphazene hydraulic fluid made by the process of claim 9.

* * * * *